United States Patent [19]

Ogilvie

[11] Patent Number: 4,501,744

[45] Date of Patent: Feb. 26, 1985

[54] SUBSTITUTED-AZA-CYTOSINE COMPOUNDS AND ANTI-VIRAL USES THEREOF

[75] Inventor: Kelvin K. Ogilvie, Candiac, Canada

[73] Assignee: ens BIO LOGICALS Inc., Toronto, Canada

[21] Appl. No.: 518,196

[22] Filed: Jul. 28, 1983

Related U.S. Application Data

[63] Continuation-in-part of Ser. No. 302,790, Sep. 16, 1981, which is a continuation-in-part of Ser. No. 187,631, Sep. 16, 1980, Pat. No. 4,347,360.

[51] Int. Cl.³ .................. C07D 251/10; A61K 31/53
[52] U.S. Cl. .................................. 514/245; 544/194; 544/211
[58] Field of Search ................. 544/194, 211; 424/249

[56] References Cited

U.S. PATENT DOCUMENTS 4,171,431 10/1979 Skulnick ........................... 544/194

4,347,360 8/1982 Ogilvie ............................. 544/276

FOREIGN PATENT DOCUMENTS 0049072 4/1982 European Pat. Off. ............ 544/276

*Primary Examiner*—Donald G. Daus
*Assistant Examiner*—S. A. Gibson
*Attorney, Agent, or Firm*—Fleit, Jacobson, Cohn & Price

[57] ABSTRACT

Nucleoside analogues having a ring-open structure, of general formula:

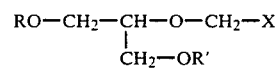

where R and R' may be hydrogen, silyl groups, substituted alkyl groups, benzyl groups and the like, and X is an optionally substituted pyrimidine or triazine base, exhibit anti-viral activities e.g. against herpes simplex virus and cytomegalo-virus at non-toxic levels.

5 Claims, No Drawings

SUBSTITUTED-AZA-CYTOSINE COMPOUNDS AND ANTI-VIRAL USES THEREOF

CROSS REFERENCE TO RELATED APPLICATIONS

This is a continuation-in-part of application Ser. No. 302,790, filed Sept. 16, 1981, pending said application Ser. No. 302,790 itself being a continuation-in-part of application Ser. No. 187,631 filed Sept. 16, 1980 and now issued as U.S. Pat. No. 4,347,360, issued Aug. 31, 1982.

BACKGROUND OF THE INVENTION

This invention relates to novel compositions and chemical compounds and processes for their preparation. More particularly, it relates to novel ring-open nucleoside and nucleotide analogues and the like, which show bioregulation activity, e.g. antiviral activity and processes for their synthesis.

BRIEF REFERENCE TO THE PRIOR ART

Nucleosides comprise a D-ribose or 2-deoxy-D-ribose sugar unit, chemically bonded to a purine or pyrimidine base selected from adenine, cytosine, guanine, thymine and uracil, via a nuclear nitrogen atom of the base. Since they are units of nucleic acids found naturally in living cells, it has been speculated previously that nucleosides and nucleotides and their related analogs might have potential as chemotherapeutic agents. Any practical value they may have, however, is often greatly reduced by their ready deamination in vivo by deaminases.

There have been several patents and publications of such compounds and chemotherapeutic activities thereof recently, including the following:

U.S. Pat. No. 4,199,574 Schaeffer, issued Apr. 22, 1980, and related patents deriving from the same original application, disclose a wide variety of compounds said to be useful in antiviral treatments, extensive testing of one of which compounds, namely acycloguanosine or acyclovir, 9-[2-hydroxyethoxymethyl]guanine, has been reported in the literature;

U.S. Pat. No. 4,347,360 Ogilvie (issued on the parent application Ser. No. 187,631 referred to above) discloses compounds such as 9-[[2-hydroxy-1-(hydroxymethyl)ethoxy]-methyl]adenine and analogues thereof, as active against herpes simplex virus.

SUMMARY OF THE INVENTION

The present invention relates to antivirally active pyrimidine and triazine nucleoside analogues, processes for their preparation, and pharmaceutically acceptable compositions thereof for administration to mammals to treat viral infections. The nucleoside analogues of the present invention are N-substituted pyrimidine or triazine compounds corresponding to the general formula:

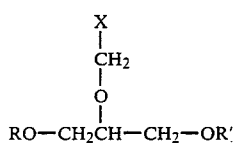

(I)

wherein X represents a uracil group, a 5-fluorouracil group, a cytosine group, or a 5-azacytosine group; and R and R' are independently selected from hydrogen, benzyl and tert. butyldimethylsilyl.

It will be appreciated that the compounds according to the present invention are closely analogous in structure and groupings to naturally occurring nucleosides and nucleotides. The essential chain arrangements and lengths are maintained. The appropriate O and OH functional groups, which in biological environments actively bind to biological centers, are maintained in their natural sequences and disposition relative to the base, but optionally modified with "protecting" groups. Indeed, the groups adjacent to the bases are so similar in chemical constitution to deoxyribose compounds that they can assume the essential conformation of the deoxyribose ring under appropriate conditions. The fundamental difference is that the compounds of the present invention lack the structural rigidity of the carbohydrate ring, which renders them unpredictably different in properties and behaviour. Also, the C-4' position is not chiral, in compounds of formula I, so that stereoisomers do not arise. Each hydroxyl is primary. There can be no syn-anti isomerism about the glycosidic bond.

Compounds of general formula I may be made by coupling the appropriately halogenated base with the appropriate alkyl residue. The synthesis my be initiated by treating, 1,3-dichloro-2-propanol with sodium benzylate under a nitrogen atmosphere followed by trioxymethylene and HCL to prepare the chloromethoxy derivative of 1,3-dibenzyloxy-2-propanol, care being taken to remove excess water. This derivative may be coupled to the appropriately protected pyrimidine or triazine base, in DMF using triethylamine as acid scavenger. The dibenzyl product so formed may be debenzylated to give a compound of formula I, e.g. with hydrogen over palladium oxide in methanol. Protecting groups, if desired, are put on by standard, known methods. Alternatively, halogenated alkyl residues may be coupled with halogenated or non-halogenated pyrimidine or triazine base compounds.

Compounds according to the present invention show anti-viral activity, accompanied by low cell toxicity, rendering them potentially useful in therapeutic compositions to combat specific viral invaders of living mammalian cells. For example, the compound 5-aza-1-[[1-hydroxymethyl(2-hydroxy)ethoxy]methyl]cytosine is active against herpes simplex virus HSV, and against cytomegalovirus $CMV_3$ at a dosage level at which it is non-toxic to mammalian cells.

Certain compounds of the aforementioned formula I in which the pyrimidine or triazine base group X is substituted on the nucleus are also of interest as potential pharmacological agents e.g. anti-virals. Specific such compounds are those in which X represents uracil substituted at the 5-position with fluoro or hydroxymethyl.

It will of course be understood that the present invention extends to cover pharmaceutically acceptable salts of the compounds described herein.

Compounds according to the present invention may be administered to a patient parenterally, interthecally applied topically as ointment, cream, aerosol or powder, or even on occasion given as eye or nose drops or orally. In general, methods of administration and dosage formulations thereof follow the known, published methods used with known antiviral drugs such as acycloguanosine, Ara-A and Ivdr. Effective unit doses for administration of the compositions interthecally or parenterally, calculated as free base, are suitably in the range from about 0.1–100 mg per kg mammal body weight, most suitably in the 0.5–20 mg per kg mammal body weight, and most preferably about 5 mg per kg, on the basis of a dosage administered from 2–4 times per day.

Orally administrable compositions are preferably in fine powder or granule form, with diluting and/or dispersing and/or surface active agents, e.g. in water or in a syrup dispersion, or as tablets or capsules. Solutions of the compounds in distilled water or saline, e.g. isotonic solutions and optionally buffered with phosphate, of concentration 1–20% preferably 2–15% and most preferably around 10%, are suitable for parenteral or intrathecal administration. Ointments (topical or cream) may be compounded for treatment of external infections, e.g. with an oil in water cream base, in a concentration of from about 0.1–10% preferably up to about 3%, most preferably about 1% w/v active ingredient. They may be compounded with paraffin oil, with petrolatum to form emulsion optionally with a surfactant for stabilizing purposes, or with dimethyl-sulfoxide.

The invention is further illustrated in the following non-limitative examples.

EXAMPLE 1

Preparation of 1-[[2-benzyloxy-1-(benzyloxymethyl)ethoxy]methyl]-5-fluorouracil

5-Fluorouracil (1.0 g, 0.0077 mole) and some crystals of ammonium sulfate were suspended in 1,1,1,3,3,3-hexamethyldisilazane (HMDS) (15 g) and brought to reflux with stirring. After 50 minutes the base had dissolved and the excess HMDS was evaporated under reduced pressure to yield syrup of silyl-protected base (structure not determined). The syrup was dissolved in 1,2-dichloroethane (80 ml) and anhydrous stannic chloride (0.4 ml) was added. 1,3-Dibenzyloxy-2-chloromethoxy propane (0.007 m mole) from a stock solution was added and the solution was stoppered and allowed to stand at room temperature overnight. The reaction mixture was shaken with aqueous sodium bicarbonate and the phases were separated. The aqueous phase was extracted with chloroform. The combined organic phases were washed once with water, dried with anhydrous sodium sulfate and evaporated under reduced pressure to yield 4.57 g of material. The nmr spectrum of the crude material suggested that the proportion of desired compound in the mixture was 88%. The material was mixed with 15 g of silica (Fisher-S-662) and applied to a silica column (93×2.0 cm). The column was eluted with 1% methanol in chloroform (250 ml), 3% methanol in chloroform (200 ml), and 5% methanol in chloroform (700 ml). When colored material began to appear fractions were collected and the first 16 test tubes contained the desired material. The fractions were individually evaporated to syrups which on standing overnight crystallized. Some methanol was added, the crystals were broken up and the solvent was removed with a pasteur pipet. The crystals were washed once with methanol to yield 0.886 g of crystals and 2.231 g of mother liquor residues. The residues were crystallized from carbon tetrachloride and the resultant mother liquor residues were applied to preparative tlc plates and eluted with 5% methanol in chloroform. Eventually 1.81 g (0.0044 mole, 62%) of crystalline 1-[[2-benzyloxy-1-(benzyloxymethyl)ethoxy]methyl]-5-fluorouracil was obtained. An analytical sample was obtained by recrystallizing the above material (tlc still showed an impurity) from a minimum of hot ethanol. The crystals gave: mp. 84°–86° C. and UV (EtOH) spectrum with $\lambda_{max}$265 nm.

The resultant compound, hereinafter referred to as 5F-benzyl-U*, has the structural formula:

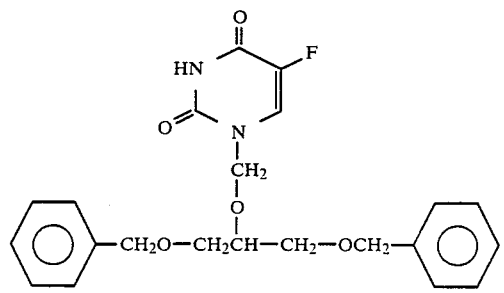

EXAMPLE 2

Preparation of 5-Fluoro-1-[[2-hydroxy-1-(hydroxymethyl)ethoxy]methyl]-uracil 5F-benzyl-U* prepared as described in Example 1 (0.656 g, 0.00158 mole) was dissolved in ethanol (26 ml). Fresh palladium black (10 ml) was added, followed by cyclohexene (13 ml). After half-hour, tlc showed that most of the starting material was gone but there was still a fair amount of monobenzyl compound present. After 5 hours tlc showed that the reaction was complete and the mixture was filtered and the Pd black was washed with ethanol. The solution was evaporated under reduced pressure to yield 0.413 g of syrup which crystallized after the addition of some methanol. The sample was dissolved in 3 ml of hot ethanol and then the volume was reduced to 1 ml by blowing with nitrogen. The resultant crystals (contained in a Greg tube) were washed 3 times with ethanol and the residual solvent was removed by centrifugation to yield 0.185 g (0.00079 mole, 50%) of crystals. The mother liquor yielded another 0.089 g (0.00038 mole, 24%) of crystals. A second recrystallization gave mp. 126°–128° C. and a UV spectrum (EtOH) $\lambda_{max}$266 nm. The nmr spectrum in $DC_3OD$ and TMS gave: 3.58 (m, 5 H, —$CH_2CH\ CH_2$—), 5.28 (s, 2 H, $OCH_2N$), 7.85 (d, 1 H, $J_{F6}$=6.0 Hz, H-6).

The resultant compound, hereinafter referred to as 5FU*, has the structural formula:

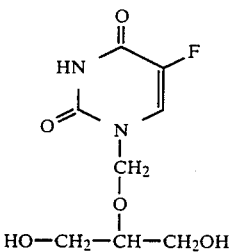

EXAMPLE 3

Preparation of 5-aza-1-[[1-hydroxymethyl-[2-hydroxyl]-ethoxy]methyl]cytosine

5-Azacytosine (5.0 g, 0.0446 mole) and ammonium sulfate (100 mg) were suspended in HMDS (40 ml) and brought to reflux with stirring. After 20 minutes more ammonium sulfate (100 mg) was added and after a further 20 minutes, under reflux the mixture became clear. The excess HMDS was evaporated under reduced pressure to yield a white solid, silyl-protected 5-azacytosine, which was used without further purification. The solid was dissolved in 1,2-dichloroethane (100 ml) and anhydrous stannic chloride (3.5 ml) was added. Then 1,3-dibenzyloxy-2-chloromethoxy propane (0.040 mole) was added and the solution was stirred at room temperature for 14 hours. The reaction solution was poured into aqueous sodium bicarbonate, diluted with chloroform and shaken. The resultant precipitate was removed by filtration through celite. The phases were separated. The aqueous phase was extracted once with chloroform. The organic phases were combined, washed once with water, dried with anhydrous sodium sulfate and evaporated to yield 15 g of syrup. The syrup was dissolved in chloroform (20 ml) and applied to a tlc silica column (14.5×6.5 cm). The column was first eluted with chloroform (450 ml). The solvent was changed to 5% methanol in chloroform and the collection of fractions (10-15 ml) was begun. The desired compound 5-aza-1-[[2-benzyloxymethyl-[1-benzyloxy]-ethoxy]methyl]cytosine was found in three groupings of fractions which were: 40–42 (1.48 g), 43–62 (8.17 g) and 63–79 (0.42 g). The groupings were dissolved in 2.3 ml, 12 ml and 1.5 ml of hot ethanol respectively and seeded. The second sample yielded 5.292 g of crystals whereas the other two samples gave few crystals. Therefore the first and third sample were combined with the mother liquor of the second sample and applied to a short silica column (4.0×6.3 cm) and first eluted with chloroform (125 ml) and then with 5% methanol in chloroform when the collection of fractions (20 ml) was begun. The desired material appeared in fractions 7-8 (1.35 g) and 9-11 (1.9 g). The 1.9 g sample was dissolved in ethanol (3 ml) and 0.917 g of crystals resulted. The yield of compound was 6.209 (0.0157, 39%). The crystals (6.209 g) were augmented by crystals (1.461 g) from another experiment and recrystallized from ethanol (10 ml) to give 6.95 g of white crystals. A sample was recrystallized twice from ethanol and it gave: mp 120°–122.5° C. The UV spectrum gave: $\lambda_{max}$ (EtOH) 228, 236, (H$_2$O) 241, (pH 1) 251, (pH 13) 250. The namr spectrum (CDCl$_3$) gave: 3.52 (d, 4 H, J=5.5 Hz, CH$_2$CHCH$_2$—), 4.02 (m, 1 H, —CH$_2$CHCH$_2$—), 4.45 (s, 4 H, 2×PhCH$_2$—), 5.30 (s, 2 H, OCH$_2$N), 7.27 (m, 11 H, 2×PhCH$_2$—), 8.07 (s, 1 H, H-6).

The above produced compound 5-aza-1-[[2-benzyloxymethyl[1-benzyloxy]-ethoxy]methyl]cytosine (6.432 g), 0.0162 mole was dissolved in ethanol (200 ml, warmed). Palladium oxide (8 g) was added followed by cyclohexene (100 ml). The stirred mixture was brought to reflux and 3 hours later tlc suggested that the reaction was slow. Therefore fresh palladium oxide (2 g) was added and reflux was continued. After a total time of 22 hours some material had precipitated out but the tlc still showed some starting material and the monobenzyl analogue. The material was filtered and the residue was washed with hot 95% ethanol until no more white precipitate was present. The filtrate and washings were combined and evaporated to yield about 4.5 g of material. The material was recrystallized from hot ethanol and some water (to help dissolve) to yield slightly greenish crystals (0.816 g, 0.00377 mole, 23.3%) which gave mp, 181°–5° C. and the filtrate was green. The filtrate was evaporated and the residue was dissolved in hot ethanol (3.5 ml) and seeded. Crystals did not form.

The material was shaken with water and chloroform and the phases were separated. The aqueous phase was co-evaporated with ethanol to yield 2 g of material. Crystallization in the usual way was not successful. The tlc showed a number of components with the desired compound comprising about 30-40% of the mixture. The material was applied to 4 prep. tlc plates and developed with 50% methanol in chloroform. The desired band was eluted with 25% methanol in chloroform to yield 0.5 g of material. Crystallization in the chloroform to yield 0.5 g of material. Crystallization in the usual way yielded only a trace of crystals. The first crop of crystals were recrystallized from water (1 ml) and ethanol (7 ml) to give white crystals which gave: mp 189.5°–191° C. the desired compound gave UV spectrum: $\lambda_{max}$ (EtOH) 220 nm, (H$_2$O) 220, 245S, (pH 1) 250 (pH 13) 248. The nmr spectrum (CD$_3$OD+5 drops DMSO-d6+TMS) gave: 3.43-3.83 (m, 5 H, —CH$_2$CHCH$_2$—), 5.37 (s, 2 H, OCH$_2$N), 8.27 (s, 1 H, H-6).

The resultant compound is 5-aza-1-[[1-hydroxymethyl-[2-hydroxy]-ethoxy]methyl]cytosine, hereinafter referred to as 5-aza-C*, has the structural formula:

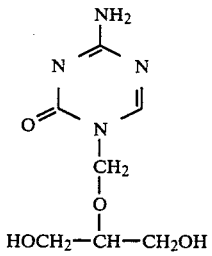

EXAMPLE 4

Preparation of 1-[[2-benzyloxy-1-(benzyloxymethyl)]ethoxymethyl]-cytosine

Cytosine (5.0 g, 0.045 mole) was suspended in 1,1,1 3,3,3-hexamethyldisilazane (80 ml, 60 g HMDS) and several crystals of ammonium sulfate were added (modeled on: G. Ritzmann & W. Pfleiderer, Chem. Ber. 106, 1401 (1973)). The stirred mixture was protected from moisture and refluxed until a clear solution was obtained. If a clear solution was not obtained after one-half hour of reflux the addition of more ammonium sulfate gave a clear solution after another 10 minutes of reflux. The clear hot solution was connected to a water aspirator and the excess HMDS was carefully removed on a hot water bath to yield a white solid which was used in the next step without purification.

The 2,4-bis-(trimethylsilyl)cytosine was dissolved in dry DCE (200 ml) and stannic chloride (3.4 ml, 29.1 moles anhydrous freshly distilled) was added. Then 40 g of stock chloride solution, namely 1,3-dibenzyloxy-2-chloromethoxy propane was added and the yellow solution was allowed to stand overnight at room temperature (modeled on B. U. Niedballa & H. Verbruggen, Angew. Chem.

The resultant product is 1-[[2-benzyloxy-1-(benzyloxymethyl)]ethoxymethyl]cytosine, hereinafter referred to as dibenzyl C*, of structural formula:

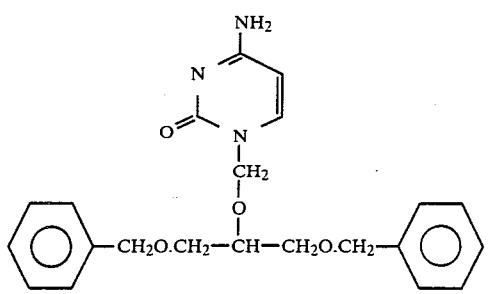

EXAMPLE 5

Testing and evaluation of compounds against herpes virus

Herpes simplex virus (HSV) strains were grown and titrated at 36° C. in human fetal fibroblasts derived from fetal tissues, and used for virus work before the tenth passage. Cells were grown and maintained in basal medium Eagle (BME; Auto-Pow, Flow Laboratories) supplemented with 0.112% sodium bicarbonate, 2 mM l-glutanine, 2 mg neomycin per 100 ml and 5–20% calf serum. 5% BME, as described hereafter, indicates medium containing 5 ml of calf serum in a total volume of 100 ml.

The titer of the HSV strains is determined by a plaque titration method (Roizman & Roane, "Virology", 15, 75–79, 1961). Tissue culture dishes are seeded with cells and used for assays when approximately 75% monolayer. Volumes (0.2 ml) of logarithmic dilutions of the strain are inoculated onto each of two tissue culture dishes, and adsorbed for 1 hr. with intermittent shaking, the inoculum removed, and 2 ml of 5% BME containing 0.5% human immune serum globulin added. After a 48 hour incubation period at 36° C. in a 5% $CO_2$ atmosphere, the overlay medium is removed and the cell sheets stained with a 0.05% aqueous crystal violet solution. The number of plaques is counted, the duplicates averaged, and the number of plaque-forming units calculated.

The compounds are tested for activity against the herpes simplex strains using a stock solution of each compound freshly prepared by dissolving 1.2 mg in BME. Appropriate dilution of each compound are made in 5% BME containing 0.5% human immune serum globulin just before usage.

Tissue culture dishes (35 by 10 mm) with approximately 75% cell monolayer are inoculated with approximately 50 plaque-forming units of HSV per 0.2 ml, and the virus adsorbed for 1 hour, with intermittent shaking. After removal of the inoculum, 2 ml of 5% BME with 0.5% immune globulin and three-fold dilutions of the appropriate drug are added. One set of dishes receives no drug and is used as a control. After a 48-hour incubation period, at 36° C. in a 5% $CO_2$ atmosphere, the overlay medium is removed, the cells stained as described above, and plaques counted. The counts of replicate plates are averaged, and the number of plaques emerging in the presence of each drug dilution is calculated. The reduction in plaque size caused by the concentration of the drug, as compared with the relevant control, is also measured, visually. A reduction in plaque number indicates that the added compound is preventing the reproduction of the viral cells. A reduction in the area of the growing plaque indicates inhibition of plaque growth, i.e. inhibition of viral reproduction, caused by the drug.

The compound of Example 3, 5-aza-C*, showed high activity against the HSV. It reduced plaque size by 25% at 5 ugm/ml, by 50% at 30 ugm/ml, and by 75% at 110 ugm/ml. It reduced plaque numbers by 25% at 8 ugm/ml, by 50% at 30 ugm/ml and by 75% at 140 ugm/ml. It showed no evidence of toxicity at concentrations as high as 304 ugm/ml.

The compound of example 4, dibenzyl-C*, m also exhibited activity against HSV, but to a lesser extent.

The compound of example 1, 5F-benzyl-U*, showed activity against HSV, reducing plaque size by 25% at 10 ugm/ml, by 50% at 50 ugm/ml, and reducing plaque numbers by 25% at 70 ugm/ml, by 50% at 110 ugm/ml. It showed no evidence of toxicity up to concentrations of 110 ugm/ml.

EXAMPLE 6

Testing and evaluation for activity against cytomegalovirus

The compounds of example 3, (5-aza-C*) was tested in vitro for activity against cytomegalovirus, CMV, in mammalian cells. Human fetal fibroblast (lung) HFF cells were used, in generally standard viral plaque titration methods.

CMV is a virus which can infect and replicate in human cells, and for which there is currently no effective curative on the market. CMV infections can have extremely serious consequences. Perhaps the most serious occurs when a mother, in the first trimester of pregnancy, is infected by CMV for the first time. When this occurs, the virus enters her blood stream and is conveyed through the placenta and the umbilical cord to the fetus or embryo. Then the virus replicates in many organs of the fetus or embryo causing developmental damage. The problem is particularly severe in the central nervous system when development of nerve tissue is affected. Such women are at high risk of delivering a newborn with severe CMV disease, which may manifest itself in fatality of the fetus or embryo. If the disease is contracted after the first trimester, the intensity of the disease diminishes progressively until full term of pregnancy. The range of difficulties include mental retardation and limited physical development.

An additional problem area is that of kidney transplants. Kidney transplant failure as a result of CMV infections is at least as serious a problem as are tissue typing problems.

Human fetal fibroblast (lung) HFF cells were used, in generally standard viral plaque titration methods. The cells were grown and maintained in Basal Medium Eagle (BME) supplemented with 0.112% sodium bicarbonate, 2 mM L-glutamine, 2 mg % neomycin and 20% (vol/vol) calf serum.

A viral plaque titration method (Roizman & Roane, 1961) was used to determine the virus titre of the CMV. 35 mm tissue culture plates were seeded with HFF 36 P5 and grown to 50–70% monolayer. CMV infected cells which had been frozen in single cell suspension containing 7.5% dimethylsulfoxide DMSO in complete BME, then revived, were diluted in complete BME.

The supernatant was removed from the plates, and the cells were inoculated with 0.2 ml diluted CMV infected cells per plate, making about 3000 focal units per plate. Drug dilutions were also made in complete BME. Half-log unit dilutions were made for titration of drug efficacy. Control plates received no infected cells and/or no drug.

The cells were incubated for 72 hours at 37° C. in 5% carbon dioxide atmosphere. At 75 hours, the number of CMV infected foci (microplaques) was quantitated using enzyme linked immunosorbent assay (ELISA) using as an enzyme tag horseradish peroxidase and DAB substrate so as to stain the infected foci with a brown precipitate.

In this assay, the complete BME was removed from the plate, and the plate was washed three times with phosphate buffered saline (PBS). The cells were fixed for 4 minutes with 95% methanol. Then the methanol was removed and the plate again washed three times with PBS and the PBS removed.

CMV-positive human serum was diluted 1:10 with PBS, and 0.2 ml of the diluted serum was put in each plate and the plate shaken for 30 minutes. The serum dilution was then removed, and the plate washed five times with PBS. Goat anti-human globulin tagged with horseradish peroxidase was diluted 1:30 in PBS and 0.2 ml of the conjugate put on each plate. The plates were shaken for 30 minutes. Then the conjugate was removed from each plate, the plates washed with PBS. At this point, 2 mls DAB substrate is added with hydrogen peroxide and incubated for approximately 30 minutes at room temperature, the substrate removed and the plates examined at low magnification in a light microscope. Plaques were counted, and numbers of plaques per microscopic field determined.

The reading of the CMV assay was done by comparing no-drug controls to the drug treated plates. Total inhibition of viral plaque formation resulted in no antigen production (no brown precipitate) associated with viral infection). No inhibition by the drug resulted in antigen production, brown precipitate formation, associated with foci containing infected cells, the same as in cultures without drugs.

The results so obtained, at various drug dilutions, are plotted or semi-logarithmic graph paper to determine the effective dose of drug which reduces viral plaque formation by 50% ($ED_{50}$). The compound of example 3, namely 5-aza-C*, was found, in repeated tests, to have $ED_{50}$ in the range 1—3.2 mcg per ml.

With CMV, most of the virus is cell associated. The amount of virus thinned out in the growth medium is negligible. Viral transfer occurs when one cell touches another (contiguous spread).

I claim:

1. 5-aza-1-[[1-hydroxymethyl-(2-hydroxy)ethoxy]methyl]cytosine and pharmaceutically acceptable salts thereof.

2. 5-aza-1-[[1-hydroxymethyl-(2-hydroxy)ethoxy]methyl]cytosine.

3. A pharmaceutical composition suitable for administration to a mammal for treatment of viral infections, comprising as active ingredient a compound according to claim 1.

4. A pharmaceutical composition active in combatting herpes viral infections and consisting essentially of the effective amount of a compound according to claim 1, in admixture with a pharmaceutically acceptable carrier.

5. A method of treating herpes viral infection in a mammal, which comprises administering to the infected mammal an effective, non-toxic amount of a compound or salt according to claim 1.

* * * * *